United States Patent [19]

Grollier

[11] Patent Number: 5,167,669
[45] Date of Patent: Dec. 1, 1992

[54] COMPOSITION FOR DYEING KERATINOUS FIBERS EMPLOYING AN INDOLE DYE AND AT LEAST ONE PARA-PHENYLENEDIAMINE CONTAINING A SECONDARY AMINO GROUP AND PROCESS FOR USE

[75] Inventor: Jean F. Grollier, Paris, France

[73] Assignee: L'Oreal, Paris, France

[21] Appl. No.: 803,077

[22] Filed: Dec. 6, 1991

Related U.S. Application Data

[62] Division of Ser. No. 555,026, Jul. 20, 1990, Pat. No. 5,096,455.

[30] Foreign Application Priority Data

Jul. 21, 1989 [FR] France ............................. 89 09835

[51] Int. Cl.$^5$ ............................................. A61K 7/13
[52] U.S. Cl. ................................... 8/405; 8/406; 8/408; 8/409; 8/410; 8/415; 8/416; 8/423; 424/70
[58] Field of Search ............ 8/405, 406, 408, 409, 8/410, 415, 416, 423; 424/70

[56] References Cited

U.S. PATENT DOCUMENTS

| | | | |
|---|---|---|---|
| 3,194,734 | 7/1965 | Seemuller et al. | 8/423 |
| 4,013,404 | 3/1977 | Parent et al. | 8/423 |
| 4,690,685 | 9/1987 | Grollier et al. | 8/405 |
| 4,776,857 | 10/1988 | Carroll et al. | 8/423 |
| 4,804,385 | 2/1989 | Grollier et al. | 8/423 |
| 4,822,375 | 4/1989 | Lang et al. | 8/409 |
| 4,888,027 | 12/1989 | Grollier et al. | 8/423 |
| 4,961,925 | 10/1990 | Tsujino et al. | 8/406 |
| 5,011,500 | 4/1991 | Grollier et al. | 8/423 |
| 5,021,067 | 6/1991 | Grollier | 8/423 |
| 5,073,174 | 12/1991 | Vayssie et al. | 8/423 |

FOREIGN PATENT DOCUMENTS 2207443 2/1989 United Kingdom .

Primary Examiner—Paul Lieberman
Assistant Examiner—William S. Parks
Attorney, Agent, or Firm—Cushman, Darby & Cushman

[57] ABSTRACT

Dyeing composition for keratinous fibers, especially for human keratinous fibers, characterized in that it contains, in an aqueous medium suitable for dyeing:

a) an indole dye; and
b) a para-phenylenediamine monosubstituted on one of the amino groups, corresponding to the formula:

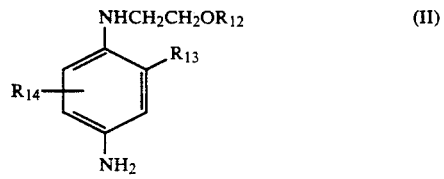

in which:

$R_{12}$ denotes a hydrogen atom or a lower alkyl group;
$R_{13}$ denotes a hydrogen atom, a lower alkyl group, a lower alkoxy group or a halogen atom; and
$R_{14}$ denotes a hydrogen atom, a lower alkyl group, a lower alkoxy group or a halogen atom; $R_{14}$ occupying any one of the remaining positions of the benzene ring; as well as the addition salts with an acid, this composition not containing an oxidizing agent other than air.

11 Claims, No Drawings

COMPOSITION FOR DYEING KERATINOUS FIBERS EMPLOYING AN INDOLE DYE AND AT LEAST ONE PARA-PHENYLENEDIAMINE CONTAINING A SECONDARY AMINO GROUP AND PROCESS FOR USE

This is a division of application Ser. No. 07/555,026, filed Jul. 20, 1990, now U.S. Pat. No. 5,096,955.

The present invention relates to new compositions for dyeing keratinous fibres, and more especially human keratinous fibres such as the hair, containing an indole dye combined with at least one para-phenylenediamine containing a secondary amino group, as well as the process for using these compositions.

The colour of the hair, skin and hairs of human origin originates mainly from melanin pigments secreted by melanocytes. These pigments of natural origin comprise, in particular, pigments referred to as eumelanins.

Their natural biosynthesis takes place in several steps through polymerization of the oxidation products of an amino acid, namely tyrosine, and one of its oxidation products is 5,6-dihydroxyindole which polymerizes, in turn, to eumelanin.

It has already been proposed in the past to dye human hair with 5,6-dihydroxyindole or indole dyes which make it possible to carry out progressive dyeing of the hair, that is to say to obtain a coloration exhibiting light hues after one application of the product up to dark hues by the superposition of different applications.

Dyeing takes place slowly, however, and to accelerate the formation of the melanin pigment in order to obtain dark hues more rapidly, different processes have already been described, in particular, in French Patents 1,133,594 and 1,166,172, employing two steps and oxidizing-gents such as hydrogen peroxide or catalytic oxidizing agents of a metallic nature.

Other oxidizing agents such as iodide ions, metal anions, nitrites, periodates and rare metal salts have also been recommended.

The Applicant has just discovered, and this forms the subject of the invention, that by using an aqueous solution containing an indole dye and at least one para-phenylenediamine monosubstituted on one of the amino groups, or its addition salts, it was possible to obtain very rapidly a progressive dyeing of the hair in natural hues ranging from blond to black.

He found, in addition, that, with the compositions according to the invention, the hair was dyed more rapidly in dark tints compared with the conventional process utilizing only 5,6-dihydroxyindole by way of a dye.

The compositions according to the invention permit a progressive dyeing of human hair in the ambient air and without the use of an oxidizing agent.

The subject of the invention is hence dyeing compositions for keratinous fibres, especially for human keratinous fibres such as human hair, containing, by way of a dye, at least one indole dye and at least one paraphenylenediamine monosubstituted on one of the amino groups.

Another subject of the invention consists of the dyeing process employing such a composition.

Other subjects of the invention will become apparent on reading the description and the examples which follow.

The dyeing composition according to the invention is essentially characterized in that it contains, in an aqueous medium suitable for dyeing, an indole dye and at least one para-phenylenediamine monosubstituted on one of the amino groups, or its addition salts with an acid.

The indole dye preferably corresponds to the formula:

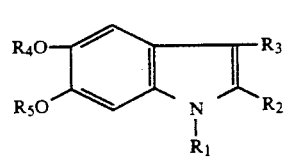

(I)

in which:

$R_1$ represents a hydrogen atom, a lower alkyl group or a group $—SiR_6R_7R_8$;

$R_2$ and $R_3$, which may be identical or different, represent a hydrogen atom or alternatively a lower alkyl group, a carboxyl group, a (lower alkoxy)carbonyl group or a group $—COOSiR_6R_7R_8$;

$R_4$ and $R_5$, which may be identical or different, represent a hydrogen atom, a linear or branched $C_1$–$C_{20}$ alkyl group, a formyl group, a linear or branched $C_2$–$C_{20}$ acyl group, a linear or branched $C_3$–$C_{20}$ alkenoyl group, a group $—SiR_6R_7R_8$, a group $—P(O)(OR_9)_2$ or a group $SO_2OR_2$, or alternatively $R_4$ and $R_5$, together with the oxygen atoms to which they are attached, form a ring optionally containing a carbonyl group, a methylene group, a thiocarbonyl group or a group:

$>P(O)OR_9$ or alternatively $>CR_{10}R_{11}$;

and $R_9$ and $R_{10}$ represent a hydrogen atom or a lower alkyl group, $R_{11}$ representing a lower alkoxy group or a mono- or dialkylamino group, $R_6$, $R_7$ and $R_8$, which may be identical or different, representing linear or branched lower alkyl groups;

and the addition salts with inorganic or organic acids as well as the corresponding alkali metal, alkaline earth metal or amine salts.

Lower alkyl or alkoxy radicals preferably denote $C_1$–$C_6$ radicals.

Among preferred compounds of formula (I), 5,6-dihydroxyindole, 2-methyl-5,6-dihydroxyindole,5-methoxy-6-hydroxyindole, (5 or 6)-acetoxy-(6 or 5)-hydroxyindole, 2-carboxy-5,6-dihydroxyindole, 3-methyl-5,6-dihydroxyindole, 2,3-dimethyl-5,6-dihydroxyindole and their salts may be mentioned more especially.

5,6-Dihydroxyindole is especially preferred, and it is used as it is or in one of its protected forms such as, for example, the diacetate.

The para-phenylenediamines monosubstituted on one of the amino groups, usable according to the invention, correspond to the formula:

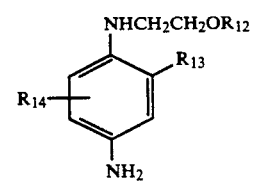

(II)

in which:

R$_{12}$ denotes a hydrogen atom or a lower alkyl group;
R$_{13}$ denotes a hydrogen atom or alternatively a lower alkyl or lower alkoxy group or a halogen atom; and
R$_{14}$ denotes a hydrogen atom, a lower alkyl or lower alkoxy group or a halogen atom; R$_{14}$ occupying any one of the remaining positions of the benzene ring.

Lower alkyl or alkoxy radicals preferably denote C$_1$–C$_4$ radicals.

Especially preferred salts of these compounds are the hydrochlorides, hydrobromides, sulphates or tartrates.

Preferred para-phenylenediamines monosubstituted on one of the amino groups, corresponding to the formula (II), are selected from compounds corresponding to the formula (II) in which R$_{12}$ denotes hydrogen or methyl and R$_{14}$ and/or R$_{13}$ denote(s) hydrogen, methyl, methoxy or a chlorine atom.

Among these compounds, those which are especially preferred are selected from N-(β-methoxyethyl)-para-phenylenediamine, N-(β-methoxyethyl)-2-methoxy-para-phenylenediamine, N-(β-hydroxyethyl)-2-methoxy-para-phenylenediamine, N-(β-hydroxyethyl)-para-phenylenediamine, N-(β-methoxyethyl)-2-chloro-para-phenylenediamine, N-(β-hydroxyethyl)-2-chloro-para-phenylenediamine, N-(β-hydroxyethyl)-2-methyl-para-phenylenediamine and their salts such as the hydrochlorides, dihydrochlorides or sulphates.

The indole dye is preferably used in the composition according to the invention in proportions of between 0.1 and 5% by weight, and more especially between 0.2 and 2% by weight, relative to the total weight of the composition.

The para-phenylenediamines monosubstituted on one of the amino groups are preferably used in the compositions according to the invention in proportions of between 0.05 and 1% by weight, and especially between 0.1 and 0.5% by weight, relative to the total weight of the composition.

The compositions according to the invention contain, in a preferred embodiment, other dyes, and in particular so-called "rapid" oxidation dyes, that is to say dye precursors having a benzene-based structure, capable of generating the coloured compound by simple oxidation in the air during the exposure time on the hair, generally less than 1 hour, and in the absence of any other oxidizing agent such as iodide ions.

The "rapid" oxidation dyes are more especially selected from trihydroxylated derivatives of benzene such as 1,2,4-trihydroxybenzene and 2,4,5-trihydroxytoluene or their protected forms such as the triacetate.

According to the invention, the rapid oxidation dyes are used in proportions of between 0.02 and 1%, and preferably between 0.05 and 0.3%, by weight relative to the total weight of the composition.

An especially preferred embodiment of the invention consists of a composition containing, in a cosmetically acceptable medium suitable for dyeing, the indole dye, and more especially 5,6-dihydroxyindole, a para-phenylenediamine monosubstituted on one of the amino groups, and more especially the preferred para-phenylenediamines mentioned above or one of their salts, and 1,2,4-trihydroxybenzene or its triacetate, in sufficient proportions for dyeing hair, and preferably those proportions mentioned above.

The aqueous medium suitable for dyeing has a pH which can vary between 4 and 11, and preferably between 6 and 9. It is adjusted to the desired value by means of alkalinizing or acidifying agents known per se, in particular those used in cosmetics when the compositions are intended for use for the dyeing of human hair.

The aqueous medium can contain, in addition, solvents which must be cosmetically acceptable when the compositions are used for the dyeing of human hair.

These solvents are used in proportions which can range up to 30% relative to the total weight of the composition, and are selected, more especially, from lower alcohols such as ethyl alcohol, propyl or isopropyl alcohol, tert-butyl alcohol; glycols such as ethylene glycol, propylene glycol; glycol ethers such as ethylene glycol monomethyl, monoethyl and monobutyl ethers, ethylene glycol monoethyl ether acetate, propylene glycol and dipropylene glycol monomethyl ethers; and methyl lactate.

Preferred solvents consist of ethyl alcohol, propylene glycol and ethylene glycol monobutyl ether.

These compositions can assume the form of a lotion, thickened or otherwise, a gel or an aerosol mousse, and can contain adjuvants well known in hair dyeing for this type of application, such as plasticizing agents, antioxidant agents, thickening agents, conditioning agents such as cationic polymers, cationic surfactants; they can also contain anionic, nonionic or amphoteric surfactants, as well as silicones, in particular volatile silicones.

The thickening agents are selected, more especially, from sodium alginate, gum arabic, guar or carob gum, heterobiopolysaccharides such as xanthan gum, cellulose derivatives such as methylcellulose, hydroxyethylcellulose, hydroxymethylcellulose, hydroxypropylcellulose and carboxymethylcellulose and various polymers having thickening functions, such as acrylic acid derivatives.

Inorganic thickening agents such as bentonite may also be used. These thickening agents are preferably present in proportions of between 0.1 and 5% by weight, and especially between 0.5 and 3% by weight, relative to the total weight of the composition.

The compositions according to the invention preferably contain antioxidant agents in sufficient proportions to avoid a premature oxidation of the dyes, and which are preferably between 0.03 and 1% by weight. They are selected, in particular, from sulphites, hydrosulphites and ascorbic acid.

An embodiment of the invention can also consist in storing the components of the composition in separate compartments, optionally protected from the air, and in carrying out the mixing of the different constituents at the time of use.

The process for dyeing keratinous fibres, and especially human hair, consists in applying on the fibres at least one composition as defined above for sufficient time to develop in the air a coloration of the keratinous fibres, and especially human hair. This dyeing takes place without the addition of an oxidation catalyst or an oxidizing agent other than the air.

According to a preferred embodiment, the composition is applied several times successively, and it is found that the tint obtained becomes increasingly dark, this also being referred to as progressive dyeing.

The application of the composition is followed after an exposure period of 5 to 50 minutes by a rinse, optional shampooing, a further rinse and drying.

The examples which follow are intended as an illustration of the invention, no limitation of the latter being, however, implied.

EXAMPLE 1

The following composition is prepared:

| | | |
|---|---|---|
| 5,6-Dihydroxyindole | | 0.21 g |
| N-(β-Methoxyethyl)-para-phenylenediamine dihydrochloride | | 0.33 g |
| Xanthan gum sold by the company Rhone Poulenc under the name RHODOPOL SC | | 2.0 g |
| Glycoside alkyl ether sold at a concentration of 60% AS by the company SEPPIC under the name TRITON CG 110 | | 3.5 g AS |
| Triethanolamine | | 4.0 g |
| Tartaric acid | | 0.3 g |
| Ethyl alcohol | | 10.0 g |
| Peservatives | qs | |
| Water | qs | 100.0 g |

An application of this composition is carried out on natural grey hair which is 90% white.

The composition is left in place for 10 minutes. The hair rinsed and dried. Hair dyed in a dark blond hue is obtained, whereas an application carried out under the same conditions with the composition containing only 5,6-dihydroxyindole leads to a golden blond, or that containing only N-(β-methoxyethyl)-para-phenylenediamine dihydrochloride does not dye.

After three applications for 10 minutes each, rinsing and drying between each application, a matt, very dark chestnut brown hue is obtained with the said composition, while with the same composition containing only 5,6-dihydroxyindole an ashen chestnut brown is obtained, and N-(β-methoxyethyl)-para-phenylenediamine dihydrochloride does not dye.

EXAMPLE 2

The following composition is prepared:

| | | |
|---|---|---|
| 5,6-Dihydroxyindole | | 0.21 g |
| N-(β-Methoxyethyl)-para-phenylenediamine dihydrochloride | | 0.33 g |
| 1,2,4-Trihydroxybenzene | | 0.18 g |
| Xanthan gum sold by the company RHONE POULENC under the name RHODOPOL SC | | 2.0 g |
| Glycoside alkyl ether sold at a concentration of 60% AS by the company SEPPIC under the name TRITON CG 110 | | 3.5 g AS |
| Triethanolamine | | 4.0 g |
| Tartaric acid | | 0.3 g |
| Ethyl alcohol | | 10.0 g |
| Preservatives | qs | |
| Water | qs | 100.0 g |

Three applications of this composition are carried out on natural grey hair which is 90% white. Each application corresponds to an exposure time of 10 minutes followed by a rinse and drying. A very dark chestnut brown hue with warm glints is obtained at the end.

EXAMPLE 3

The following composition is prepared:

| | | |
|---|---|---|
| 5,6-Dihydroxyindole | | 0.21 g |
| N-(β-Methoxyethyl)-2-methoxy-p-phenylenediamine sulphate | | 0.41 g |
| Xanthan gum sold by the company RHONE POULENC under the name RHODOPOL SC | | 2.0 g |
| Glycoside alkyl ether sold at a concentration of 60% AS by the company SEPPIC under the name TRITON CG 110 | | 3.5 g AS |
| Triethanolamine | | 4.0 g |
| Tartaric acid | | 0.3 g |
| Ethyl alcohol | | 10.0 g |
| Preservatives | qs | |
| Water | qs | 100.0 g |

Three applications of this composition are performed on natural grey hair which is 90% white, for 10 minutes each, each being followed by a rinse and drying. An ashen medium grey hue is obtained at the end, while 5,6-dihydroxyindole alone in the same vehicle leads to an ashen chestnut brown and N-(β-methoxyethyl)-2-methoxy-p-phenylenediamine sulphate alone gives a light blond with a drab hue.

EXAMPLE 4

Example 3 is reproduced by adding 0.18 g of 1,2,4-trihydroxybenzene to the composition. After three applications, a luminous medium grey is obtained.

EXAMPLE 5

The following composition is prepared:

| | | |
|---|---|---|
| 5,6-Dihydroxyindole | | 0.21 g |
| N-(β-Hydroxyethyl-2-methoxy-p-phenylenediamine sulphate | | 0.39 g |
| Xanthan gum sold by the company RHONE POULENC under the name RHODOPOl SC | | 2.0 g |
| Glycoside alkyl ether sold at a concentration of 60% AS by the company SEPPIC under the name TRITON CG 110 | | 3.5 g AS |
| Triethanolamine | | 4.0 g |
| Tartaric acid | | 0.3 g |
| Ethyl alcohol | | 10.0 g |
| Preservatives | qs | |
| Water | qs | 100.0 g |

Three applications of this composition are performed on natural grey hair which is 90% white. Each application corresponds to an exposure time of 10 minutes followed by a rinse and drying. At the end, the hue is ashen dark grey, while 5,6-dihydroxyindole alone in the same vehicle gives an ashen chestnut brown and N-(β-hydroxyethyl)-2-methoxy-p-phenylenediamine sulphate leads to an irridescent light blond.

EXAMPLE 6

The following composition is prepared:

| | | |
|---|---|---|
| 5,6-Dihydroxyindole | | 0.21 g |
| N-(β-Hydroxyethyl)-2-methyl-para-phenylenediamine sulphate | | 0.37 g |
| Xanthan gum sold by the company RHONE POULENC under the name RHODOPOL SC | | 2.0 g |
| Glycoside alkyl ether sold by the company SEPPIC at a concentration of 60% AS under the name TRITON CG 110 | | 3.5 g AS |
| Triethanolamine | | 4.0 g |
| Tartaric acid | | 0.3 g |
| Ethyl alcohol | | 10.0 g |
| Preservatives | qs | |
| Water | qs | 100.0 g |

Three applications of this composition are performed on natural grey hair which is 90% white. Each application corresponds to an exposure time of 10 minutes followed by a rinse and drying. At the end, the hue is ashen dark grey, while 5,6-dihydroxyindole alone in the same vehicle gives an ashen chestnut brown and N-(β-hydroxyethyl)-2-methyl-p-phenylenediamine sulphate gives a very slightly golden light blond.

EXAMPLE 7

The following composition is prepared:

| | | |
|---|---|---|
| 5,6-Dihydroxyindole | | 0.21 g |
| N-(β-Hydroxyethyl)-p-phenylene-diamine sulphate | | 0.35 g |
| Xanthan gum sold by the company RHONE POULENC under the name RHODOPOL SC | | 2.0 g |
| Glycoside alkyl ether sold at a concentration of 60% AS by the company SEPPIC under the name TRITON CG 110 | | 3.5 g AS |
| Triethanolamine | | 4.0 g |
| Tartaric acid | | 0.3 g |
| Ethyl alcohol | | 10.0 g |
| Preservatives | qs | |
| Water | qs | 100.0 g |

Three applications of this composition are performed on natural grey hair which is 90% white. Each application corresponds to an exposure time of 10 minutes followed by a rinse and drying. At the end, the hue is very dark chestnut brown with deep purple glints, while 5,6-dihydroxyindole alone in the same vehicle gives an ashen chestnut brown and N-(β-hydroxyethyl)-p-phenylenediamine sulphate gives a golden light blond.

EXAMPLE 8

The following composition is prepared:

| | | |
|---|---|---|
| 5,6-Dihydroxyindole | | 0.21 g |
| N-(β-Methoxyethyl)-2-chloro-p-phenylenediamine hydrochloride | | 0.33 g |
| Xanthan gum sold by the company RHONE POULENC under the name RHODOPOL SC | | 2.0 g |
| Glycoside alkyl ether sold at a concentration of 60% AS by the company SEPPIC under the name TRITON CG 110 | | 3.5 g AS |
| Triethanolamine | | 4.0 g |
| Tartaric acid | | 0.3 g |
| Ethyl alcohol | | 10.0 g |
| Preservatives | qs | |
| Water | qs | 100.0 g |

After three applications of this composition for 10 minutes each, followed by a rinse and then drying in each instance, a deep purple chestnut brown hue is obtained on permanent-waved grey hair which is 90% white, while 5,6-dihydroxyindole alone gives ashen chestnut brown under the same conditions and N-(β-methoxyethyl)-2-chloro-p-phenylenediamine hydrochloride alone gives no coloration.

EXAMPLE 9

Example 8 is reproduced, adding 0.18 g of 1,2,3-trihydroxybenzene to the composition. After three applications, a luminous deep purple chestnut brown hue is obtained.

EXAMPLE 10

The following composition is prepared:

| | | |
|---|---|---|
| 5,6-Dihydroxyindole | | 0.21 g |
| N-(β-Hydroxyethyl)-2-chloro-p-phenylenediamine | | 0.26 g |
| 1,2,4-Trihydroxybenzene | | 0.18 g |
| Xanthan gum sold by the company RHONE POULENC under the name RHODOPOL SC | | 2.0 g |
| Glycoside alkyl ether sold at a concentration of 60% AS by the company SEPPIC under the name TRITON CG 110 | | 3.5 g AS |
| Triethanolamine | | 4.0 g |
| Tartaric acid | | 0.3 g |
| Ethyl alcohol | | 10.0 g |
| Preservatives | qs | |
| Water | qs | 100.0 g |

Three applications of this composition are carried out on natural grey hair which is 90% white. Each application corresponds to an exposure time of 10 minutes followed by a rinse and drying. A deep purple chestnut brown hue is obtained at the end, while the combination of 5,6-dihydroxyindole and 1,2,4-trihydroxybenzene in the same vehicle gives an ashen dark blond and N-(β-hydroxyethyl)-2-chloro-p-phenylenediamine alone does not dye.

EXAMPLE 11

The following composition is prepared:

| | | |
|---|---|---|
| 2-Methyl-5,6-dihydroxyindole monohydrobromide | | 0.34 g |
| N-(β-Hydroxyethyl)-2-methyl-para-phenylenediamine sulphate | | 0.37 g |
| Ethyl alcohol | | 10.0 g |
| Xanthan gum sold by the company RHONE POULENC under the name RHODOPOL SC | | 2.0 g |
| Glycoside alkyl ether sold by the company SEPPIC under the name TRITON CG 110 | | 2.1 g AS |
| Tartaric acid | | 0.3 g |
| Triethanolamine | | 4.0 g |
| Preservatives | qs | |
| Demineralized water | qs | 100.0 g |

This gel is applied for 10 minutes on permanent-waved grey hair which is 90% white. The hair is rinsed and dried. After three applications, a pearlescent light chestnut brown hue is obtained on permanent-waved hair. Under the same conditions, the indole derivative gives only an ashen dark blond coloration. The para-phenylenediamine derivative, for its part, dyes in a very slightly golden light blond hue.

EXAMPLE 12

The following composition is prepared:

| | | |
|---|---|---|
| 5-Methoxy-6-hydroxyindole | | 0.23 g |
| N-(β-Hydroxyethyl)-2-chloro-para-phenylenediamine | | 0.26 g |
| 1,2,4-Trihydroxybenzene | | 0.18 g |
| Ethyl alcohol | | 10.0 g |
| Xanthan gum sold by the company RHONE POULENC under the name RHODOPOL SC | | 2.0 g |
| Glycoside alkyl ether sold by the company SEPPIC under the name TRITON CG 110 | | 2.1 g AS |

| | |
|---|---|
| Tartaric acid | 0.3 g |
| Triethanolamine | 4.0 g |
| Preservatives | qs |
| Demineralized water | qs 100.0 g |

This gel is applied for 10 minutes on permanent-waved grey hair which is 90% white. The hair is rinsed and dried. After three applications, a pearlescent golden dark blond hue is obtained. Under these conditions, the indole derivative and the para-phenylenediamine derivative hardly dye the hair. The trihydroxybenzene, for its part, dyes in a pearlescent beige light blond hue.

EXAMPLE 12

The following composition is prepared:

| | |
|---|---|
| 2-Carboxy-5,6-dihydroxyindole | 0.5 g |
| N-($\beta$-Hydroxyethyl)-p-phenylene-diamine sulphate | 0.8 g |
| Ethyl alcohol | 10.0 g |
| Sodium lauryl ether sulphate in aqueous solution containing 28% of AS | 0.2 g AS |
| Hydroxyethylcellulose sold by the company AQUALON under the name NATROSOL 250 HHR | 1.0 g |
| Glycoside alkyl ether sold containing 60% of AS by the company ROHM & HAAS under the name TRITON CG 110 | 5.0 g AS |
| Triethanolamine | qs pH 8 |
| Demineralized water | qs 100.0 g |

An application of this composition is carried out on natural grey hair which is 90% white.

The composition is left in place for 10 minutes. The hair rinsed and dried. Hair dyed in an irridescent golden ashen hue is obtained, whereas an application carried out under the same conditions with the composition containing only 2-carboxy-5,6-dihydroxyindole does not dye, or that containing only N-($\beta$-hydroxyethyl)-p-phenylenediamine sulphate leads to a golden hue.

After three applications for 10 minutes each, rinsing and drying between each application, an intense irridescent ashen hue is obtained with the said composition, while with the same composition containing only N-($\beta$-hydroxyethyl)-p-phenylenediamine sulphate a golden hue is obtained, and 2-carboxy-5,6-dihydroxyindole does not dye.

EXAMPLE 14

The following composition is prepared:

| | |
|---|---|
| 3-Methyl-5,6-dihydroxyindole | 0.8 g |
| N-($\beta$-hydroxyethyl)-2-chloro-para-phenylenediamine sulphate | 1.0 g |
| Ethyl alcohol | 10.0 g |
| Sodium lauryl ether sulphate in aqueous solution containing 28% of AS | 0.2 g AS |
| Hydroxyethyl cellulose sold by the company AQUALON under the name NATROSOL 250 HHR | 1.0 g |
| Glycoside alkyl ether sold containing 60% of AS by the company ROHM & HAAS under the name TRITON CG 110 | 5.0 g AS |
| Triethanolamine | qs pH 6 |
| Demineralized water | qs 100.0 g |

Three applications of this composition are carried out on permanent-waved grey hair which is 90% white. Each application corresponds to an exposure time of 10 minutes followed by a rinse and drying. A deep matt ashen hue is obtained at the end.

EXAMPLE 15

The following composition is prepared:

| | |
|---|---|
| 2,3-Dimethyl-5,6-dihydroxyindole | 1.5 g |
| N-($\beta$-Methoxyethyl)-p-phenylene-diamie sulphate | 0.1 g |
| Ethyl alcohol | 10.0 g |
| Sodium lauryl ether sulphate in aqueous solution containing 28% of AS | 0.2 g AS |
| Hydroxyethylcellulose sold by the company AQUALON under the name NATROSOL 250 HHR | 1.0 g |
| Glycoside alkyl ether sold containing 60% of AS by the company ROHM & HAAS under the name TRITON CG 110 | 5.0 g AS |
| Triethanolamine | qs pH 7 |
| Demineralized water | qs 100.0 g |

Three applications of this composition are carried out on natural grey hair which is 90% white. Each application corresponds to an exposure time of 10 minutes followed by a rinse and drying. An irridescent ashen dark blond hue is obtained at the end.

PREPARATION EXAMPLE 1

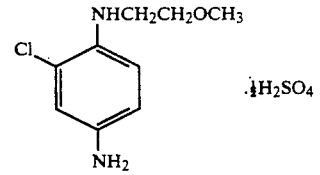

Preparation of
N-($\beta$-methoxyethyl)-2-chloro-para-phenylenediamine hemisulphate hemihydrate 1) Preparation of
4-($\beta$-methoxyethyl)amino-3-chloronitrobenzene 0.3 mol (56.2 g) of 3,4-dichloronitrobenzene in 170 ml of 2-methoxyethylamine is heated to reflux for 3 hours.

The expected product is precipitated by dilution in 500 ml of ice-cold water. After being reconverted to a paste in water and then dried, the product obtained is recrystallized from acetone. It melts at 133° C.

Analysis of the product obtained gives the following results:

| | Analysis for $C_9H_{11}ClN_2O_3$ | | | |
|---|---|---|---|---|
| | C | H | N | Cl |
| Calculated | 46.86 | 4.81 | 12.15 | 15.37 |
| Found | 46.81 | 4.99 | 12.17 | 15.17 |

2) Preparation of
N-($\beta$-methoxyethyl)-2-chloro-para-phenylenediamine hemisulphate hemihydrate 10.6 g of 4-($\beta$-methoxyethyl)amino-3-chloronitrobenzene are added portionwise to a suspension, brought to reflux, of 23 g of powdered zinc in 55 ml of ethanol and 11 ml of water to which 0.5 g of ammonium chloride has been added. 5 minutes after completion of the addition, the zinc is removed by filtration of the reaction medium while hot.

The expected product precipitates after the addition of 4.5 ml of sulphuric acid to the filtrate.

Analysis of the product recrystallized from methanol gives the following results:

| Analysis for $C_9H_{15}ClN_2O_{3.5}S_{0.5}$ | | | |
| --- | --- | --- | --- |
| C | H | N | S |
| Calculated 41.78 | 5.84 | 10.82 | 6.20 |
| Found 41.57 | 5.81 | 10.95 | 6.59 |

By dilution of the filtrate with 4 ml of concentrated hydrochloric acid, N-($\beta$-methoxyethyl)-2-chloro-para-phenylenediamine hydrochloride is prepared.

PREPARATION EXAMPLE 2

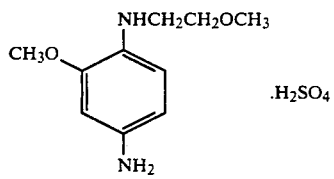

Preparation of
N-($\beta$-methoxyethyl)-2-methoxy-para-phenylenediamine sulphate 1) Preparation of
4-($\beta$-methoxyethyl)amino-3-methoxynitrobenzene 0.3 mol (56.2 g) of 4-chloro-3-methoxynitrobenzene in 170 ml of 2-methoxyethylamine is heated to reflux for 18 hours. The excess 2-methoxyethylamine is distilled off. The reaction medium is diluted with 300 g of ice-cold water.

The expected product precipitates. After recrystallization from ethanol and then from benzene, it melts at 113° C.

Analysis of the product obtained gives the following results:

| Analysis for $C_{10}H_{14}N_2O_4$ | | | |
| --- | --- | --- | --- |
| | C | H | N |
| Calculated | 53.09 | 6.24 | 12.38 |
| Found | 53.36 | 6.36 | 12.29 |

2) Preparation of
N-($\beta$-methoxyethyl)-2-methoxy-para-phenylenediamine sulphate 26.5 g of 4-($\beta$-methoxyethyl)amino-3-methoxynitrobenzene are added to a suspension, brought to reflux, of 60 g of powdered zinc in 120 ml of ethanol and 18 ml of water to which 1.2 g of ammonium chloride have been added. 5 minutes after completion of the addition, the zinc is removed by filtration. By dilution of the filtrate with 8 ml of sulphuric acid, the expected product precipitates.

After recrystallization from ethanol, the results of the analysis are:

| Analysis for $C_{10}H_{18}N_2SO_6$ | | | |
| --- | --- | --- | --- |
| | C | H | N | S |
| Calculated | 40.81 | 6.17 | 9.52 | 10.87 |
| Found | 41.00 | 6.10 | 9.38 | 10.98 |

I claim:

1. A dyeing composition for keratinous fibers comprising, in an aqueous medium suitable for dyeing said fibers,
  (a) an indole dye present in an amount ranging from 0.1 to 5 percent by weight relative to the total weight of said composition, and
  (b) a para-phenylenediamine monosubstituted on one of the amino groups and having the formula

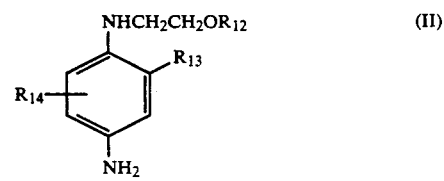

wherein
$R_{12}$ represents hydrogen or lower alkyl,
$R_{13}$ represents hydrogen, lower alkyl, lower alkoxy or halogen and
$R_{14}$ represents hydrogen, lower alkyl, lower alkoxy or halogen and occupies any one of the remaining positions of the benzene ring, and
the acid addition salts thereof,
said paraphenylenediamine being present in an amount ranging from 0.05 to 1 percent by weight relative to the total weight of said composition and said composition not containing an oxidizing agent or oxidation catalyst other than air.

2. The composition of claim 1 wherein said indole dye has the formula

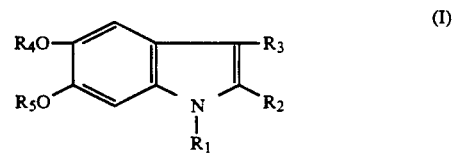

wherein
$R_1$ represents hydrogen, lower alkyl or $-SiR_6R_7R_8$,
$R_2$ and $R_3$, each independently, represent hydrogen, lower alkyl, carboxyl, (lower alkoxy) carbonyl or $-COOSiR_6R_7R_8$,
$R_4$ and $R_5$, each independently, represent hydrogen, linear or branched $C_1-C_{20}$ alkyl, formyl, linear or branched $C_2-C_{20}$ acyl, linear or branched $C_3-C_{20}$ alkenoyl, $-SiR_6R_7R_8$, $-P(O)(OR_9)_2$ or $SO_2OR_9$, or $R_4$ and $R_5$, together with the oxygen atoms to which they are attached form a ring optionally containing a carbonyl group, a methylene group a thiocarbonyl group, a $>P(O)(OR_9)_2$ group or a $>CR_{10}R_{11}$ group,
$R_9$ and $R_{10}$ represent hydrogen or lower alkyl,
$R_{11}$ represents lower alkoxy, monoalkylamino or dialkylamino,
$R_6$, $R_7$ and $R_8$, each independently, represent linear or branched lower alkyl, and the addition salts thereof with an inorganic or organic acid and the corresponding alkali metal, alkaline earth metal or amine salts.

3. The composition of claim 1 wherein said indole dye is selected from the group consisting of
5,6-dihydroxyindole,
2-methyl-5,6-dihydroxyindole,
5-methoxy-6-hydroxyindole,
5-acetoxy-6-hydroxyindole,
6-acetoxy-5-hydroxyindole,
2-carboxy-5,6-dihydroxyindole,
3-methyl-5,6-dihydroxyindole,
2,3-dimethyl-5,6-dihydroxyindole and the salts thereof.

4. The composition of claim 1 where in said paraphenylenediamine of formula II, $R_{12}$ represents hydrogen or methyl and $R_{13}$ and $R_{14}$, each independently, represent hydrogen, methyl, methoxy or chlorine.

5. The composition of claim 4 wherein said paraphenylenediamine of formula II is selected from the group consisting of
N-($\beta$-methoxyethyl)-paraphenylenediamine,
N-($\beta$-methoxyethyl)-2-methoxyparaphenylenediamine,
N-($\beta$-hydroxyethyl) paraphenylenediamine,
N-($\beta$-hydroxyethyl)-2-methylparaphenylenediamine,
N-($\beta$-methoxyethyl)-2-chloroparaphenylenediamine,
N-($\beta$-hydroxyethyl)-2-chloroparaphenylenediamine, and
N-($\beta$-hydroxyethyl)-2-methoxyparaphenylenediamine.

6. A dyeing composition for keratinous fibers comprising in a cosmetically acceptable aqueous medium
(a) 5,6-dihydroxyindole present in an amount ranging from 0.1 to 5 percent by weight relative to the total weight of said composition, and
(b) a paraphenylenediamine monosubstituted on one of the amino groups and having the formula

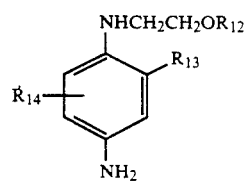

wherein
$R_{12}$ presents hydrogen or lower alkyl,
$R_{13}$ represents hydrogen, lower alkyl, lower alkoxy or halogen and
$R_{14}$ represents hydrogen, lower alkyl, lower alkoxy or halogen and occupies ny one of the remaining positions of the benzene ring, and
the acid addition salts thereof,
said paraphenylenediamine being present in an amount ranging from 0.05 to 1 percent by weight relative to the total weight of said composition and said composition not containing an oxidizing agent or oxidation catalyst other than air.

7. The composition of claim 1 which also contains a rapid oxidation dye selected from trihydroxylated derivatives of benzene and their protected derivatives, said rapid oxidation dye being present in an amount ranging from 0.02 to 1 percent by weight relative to the total weight of said composition.

8. The composition of claim 1 wherein said indole dye is 5,6-dihydroxyindole, said composition also containing 1,2,4-trihydroxybenzene or its triacetate in an amount ranging from 0.02 to 1 percent by weight relative to the total weight of said composition.

9. The composition of claim 1 wherein said aqueous medium has a pH ranging from 4 to 11.

10. The composition of claim 1 wherein said aqueous medium contains up to 30 percent of a solvent selected from an alcohol, a glycol, a glycol ether, methyl lactate and ethylene glycol mono-ethyl ether acetate.

11. The composition of claim 1 in the form of a lotion, thickened or not, a gel or an aerosol mousse.

* * * * *